United States Patent
Hajianpour

(12) 
(10) Patent No.: US 6,176,607 B1
(45) Date of Patent: Jan. 23, 2001

(54) APPARATUS FOR DISPENSING A LIQUID COMPONENT OF A TWO-COMPONENT BONE CEMENT AND FOR STORING, MIXING, AND DISPENSING THE CEMENT

(75) Inventor: Mohammed Ali Hajianpour, Coral Springs, FL (US)

(73) Assignee: Stryker Technologies Corporation, Kalamazoo, MI (US)

( * ) Notice: Under 35 U.S.C. 154(b), the term of this patent shall be extended for 0 days.

(21) Appl. No.: 09/362,246

(22) Filed: Jul. 28, 1999

Related U.S. Application Data

(62) Division of application No. 08/931,659, filed on Sep. 16, 1997, now Pat. No. 6,042,262.
(60) Provisional application No. 60/054,082, filed on Jul. 29, 1997.

(51) Int. Cl.[7] .................................................... B01F 13/06
(52) U.S. Cl. ........................ 366/139; 366/142; 366/310; 366/325.94; 366/601
(58) Field of Search .................................. 366/310, 601, 366/130, 139, 142, 189, 194, 195, 325.94; 206/219–222

(56) References Cited

U.S. PATENT DOCUMENTS

| | | | |
|---|---|---|---|
| 4,973,168 | * | 11/1990 | Chan ..................................... 206/219 |
| 5,145,250 | * | 9/1992 | Planck et al. ........................ 366/139 |
| 5,435,645 | * | 7/1995 | Faccioli et al. ....................... 366/139 |
| 5,443,182 | * | 8/1995 | Tanaka et al. . |
| 5,549,380 | * | 8/1996 | Lidgren et al. ....................... 206/222 |
| 5,551,778 | * | 9/1996 | Hauke et al. ........................ 366/139 |
| 5,588,745 | * | 12/1996 | Tanaka et al. ....................... 366/130 |
| 5,842,786 | * | 12/1998 | Solomon ............................. 366/189 |
| 5,934,803 | * | 8/1999 | Hutter ................................. 366/139 |
| 6,024,480 | * | 2/2000 | Seaton et al. ....................... 366/139 |

* cited by examiner

Primary Examiner—Charles E. Cooley
(74) Attorney, Agent, or Firm—Lerner, David, Littenberg, Krumholz & Mentlik, LLP

(57) ABSTRACT

Apparatus for storing, mixing, and dispensing a two-component bone cement includes a first component supply section, a mixing section, and a drive base. One or more ampules of the first (liquid) component, provided within the first component supply section, are broken or cut when a lever is rotated. The second (powder) component is provided within the mixing section. During the mixing process, a vacuum is applied within the mixing section, assisting in the delivery of the first component through a filter while preventing the passage of broken glass or plastic from the ampules. Mixing is done by a pair of paddles and a helical spring rotating within the mixing station, being driven in one direction, or in alternating opposite directions of rotation, by the drive base. The resulting mixture is dispensed by placing the mixing station, without the drive base and the first component supply section, into a dispensing gun, which drives a shaft moving a piston within the mixing section to dispense the mixture through a dispensing tube while collapsing the helical spring. A plug within the piston is pushed through the dispensing tube to clear the mixture remaining therein. In an alternative arrangement, mixing occurs under vacuum conditions in a bowl having an internal surface similarly scraped with a flexible wire.

40 Claims, 5 Drawing Sheets

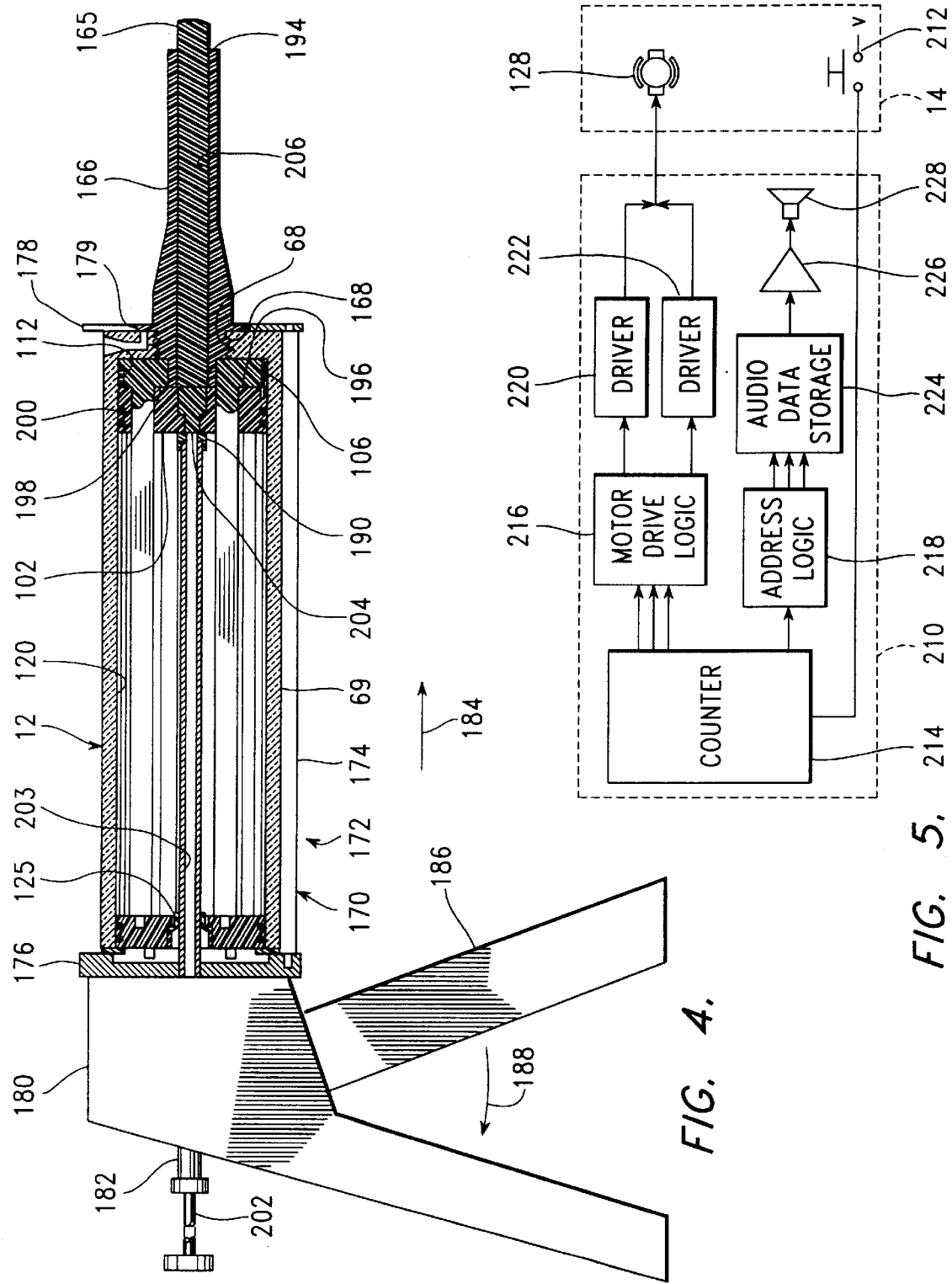

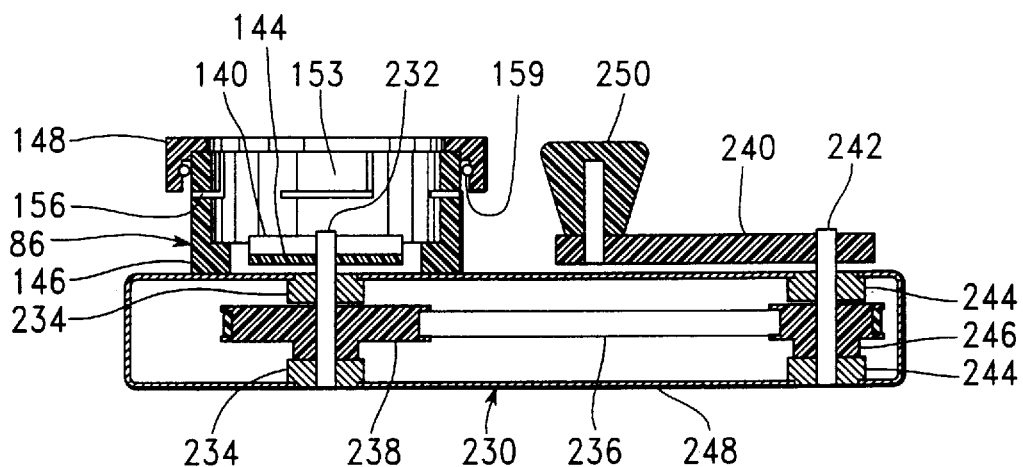
FIG. 6.
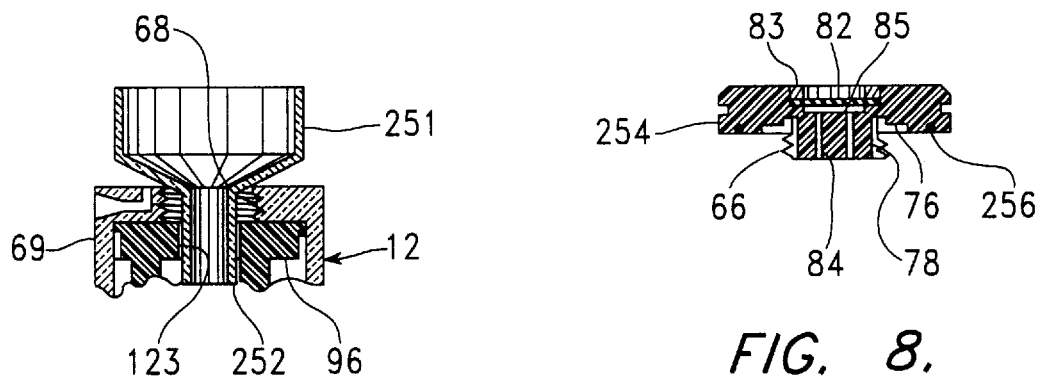
FIG. 7.
FIG. 8.
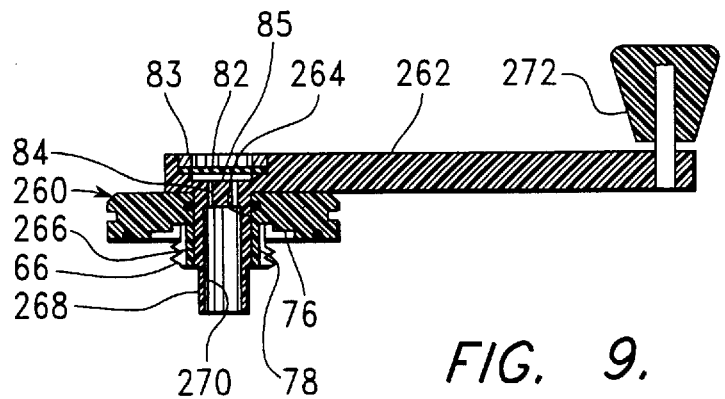
FIG. 9.

APPARATUS FOR DISPENSING A LIQUID COMPONENT OF A TWO-COMPONENT BONE CEMENT AND FOR STORING, MIXING, AND DISPENSING THE CEMENT

This application is a division of a prior filed application, Ser. No. 08/931,659, filed Sep. 16, 1997, now U.S. Pat. No. 6,042,262 which claims benefit of a prior filed provisional application, Ser. No. 60/054,082, filed Jul. 29, 1997.

BACKGROUND OF THE INVENTION

1. Field of the Invention

This invention relates to an apparatus and method for supplying, mixing and dispensing a two-component bone cement.

2. Background Information

In many orthopedic surgical procedures, it is necessary to fix a prosthesis, such as an artificial joint, to living bone within a patient. Such procedures are used to treat osteoarthritis, rheumatoid arthritis, traumatic arthritis, avascular necrosis secondary to sickle cell anemia or collagen disease, severe joint destruction secondary to trauma or other conditions, and the revision of previous arthroplasty procedures. For such procedures, the use of a bone cement, in the form of an acrylic material comprising a reaction product of a methyimethacrylate monomer and a polymethyl-methacrylate-methylmethacrylate-styrene copolymer, is indicated. The use of such a bone cement is also indicated for the fixation of pathological fractures where loss of bone substance or recalcitrance of the fracture renders more conventional procedures ineffective. A bone cement of this type allows the seating and securing of a prosthesis to bone, and, when polymerization is complete, provides a buffer for the even distribution of weight and other stresses between the prosthesis and bone.

A bone cement of this type is available from Howmedica, a Division of Pfizer Hospital Products Group, Inc., Rutherford, N.J., under the registered trademark SURGICAL SIMPLEX® P, a radiopaque bone cement. This material is packaged as two separate, sterile components, which must be thoroughly mixed immediately before the cement is applied in surgery.

The first of these components is a colorless, flammable liquid, having a sweet, slightly acrid odor, supplied in an ampule containing a 20-ml full dose or a 10-ml half dose. This liquid component is composed of methyl methacrylate monomer, 97.4 percent by volume, N, N-dimethyl-p-toluidine, 2.6 percent by volume, and hydroquinone, 75±15 parts per million. The hydroquinone is added to prevent premature polymerization, which may otherwise occur under certain conditions, such as exposure to light or elevated temperatures. The N, N-dimethyl-p-toluidine is added to promote the cold curing of the mixed compound. This liquid component has been sterilized by membrane filtration.

The second of these components is a finely divided white powder, supplied in a packet containing a 40-g full dose or a 20-g half dose. This powder component is composed of polymethyl methacrylate, 15 percent by weight, methyl methacrylate-styrene copolymer, 75 percent by weight, and barium sulfate, U.S.P, 10 percent by weight. The barium sulfate, U.S.P. is added to provide radiopacity. This powder component is sterilized by gamma irradiation.

When these liquid and powder components are mixed, an exothermic polymeric reaction forms a soft, pliable, dough-like mass. Within a few minutes, as this reaction progresses, a hard, cement-like complex is formed. These components may be manually mixed in a stainless steel or other inert container, into which the entire content of the powder component package is poured. The entire liquid content of the ampule is added to this powder, and the mixture is stirred with a sterile stainless steel spatula, or other suitable inert device, until the powder is completely saturated with the liquid. The mixture is then administered to the bone under pressure through a suitable sterile injection device, after stirring for 1 to 1 ½ minutes in an operating room temperature of 75° F.

Alternately, the mixture may be manually administered, after stirring is continued until a dough-like mass is formed. After a mixing and kneading process at least 4 minutes in duration, the fact that the mass does not stick to the rubber gloves of the operator provides an indication that the mass is ready for manipulation. The mixed and kneaded cement is applied to the bone manually or through the use of a suitable sterile pressurizing device, with the correct working consistency of the cement for application to bone being best determined by the experience of the surgeon.

Because the mixed cement sets so quickly, the two components are almost always mixed in the sterile environment of the operating room by a surgical assistant. A number of precautions must be followed. For example, the liquid component is a powerful lipid solvent, which has caused contact dermatitis in susceptible individuals. It is recommended that an individual working with these materials should wear two pairs of surgical gloves, while strictly adhering to established procedures, so that the compound dos not come into direct contact with sensitive tissues, and so that is not absorbed in his body. During the mixing of these materials, and during their chemical reaction, noxious and toxic vapors may be produced, which preclude, for example, the wearing of soft contact lenses in the operating room where the cement is being prepared. Although there is no present report indicating that the vapor is harmful, it is unpleasant, and it disturbs the breathing of many individuals. It is therefore particularly desirable to minimize the contact of operating room personnel with the vapor and to minimize the release of the vapor into the atmosphere.

Care must also be taken in the mixing of the liquid and powder components to ensure that the entire contents of the ampule and pouch are utilized. The mixing of these components should be thorough and vigorous. Data from in vitro studies have shown that monomer loss is related primarily to the frequency of stirring and secondarily to the duration of stirring. Adverse reactions affecting the cardiovascular system have been attributed to a leakage of unpolymerized liquid monomer into the circulatory system. On the other hand, caution should be taken to avoid kneading the cement too long, in order to avoid progression of the polymerization process to the point at which the cement is not adequately soft and pliable to obtain good filling of the bone cavities and fitting to the prosthesis.

DESCRIPTION OF THE PRIOR ART

In the U.S. Patent art, a number of examples describe apparatus for mixing the components of bone cement in an evacuated chamber. In a first example of such apparatus, U.S. Pat. No. 4,185,072 to Puderbaugh et al. discloses a manually-operated combination mixing-reaction apparatus including a housing with an intermediate cavity shaped generally as a hemispherical bowl. An annular pattern of channels extending around the top of this intermediate cavity is connected with a lower cavity, in which a vacuum is drawn. A cover placed atop this structure provides a central bearing for a shaft extending downward to mixing vanes and upward to a pivoting handle. One mixing vane includes an arcuate portion rotated close to the hemispherical wall of the intermediate cavity, while the other mixing vane includes an arcuate portion extending midway between the wall and the vertical axis of rotation of the vanes.

Another example of such apparatus is found in U.S. Pat. No. 5,348,391, to Murray, which describes a rotary mixer having a pair of mixing arms. The arms follow continuous paths within a cylindrical container in which the cement is mixed, with each such path having a plurality of loops at the chamber and curved portions extending across the chamber between loops. This type of movement is accomplished by driving the arms in a planetary motion, with rotation of a planetary shaft to which the arms are attached occurring within a plate rotated about a central drive shaft turned with a crank extending above the chamber. The planetary rotation is caused by the meshing engagement of several gears. The arms move through the cement, breaking bubbles and thoroughly mixing the cement components. An opening at the top of the chamber is connected to an outer chamber in which a vacuum is drawn.

While the devices of U.S. Pat. Nos. 4,185,072 and 5,348,391 each contain vanes or arms operating in a paddle fashion to mix the cement components, the contact between these movable mixing devices and the wall of the container in which the cement is mixed is limited, if such contact occurs at all. It is particularly difficult, using mass production methods, to form a container of this sort with accurate and repeatable internal dimensions. Since the vanes and arms of these patented prior art devices are relatively rigid, clearance must be provided between these vanes and arms and the walls, in order to prevent the jamming of the mixing mechanism due to mechanical interferences. Thus, what is needed is a mixing device presenting a flexible surface to slide and scrape along the surface of the mixing chamber.

Furthermore, to facilitate the maintenance of sterile conditions in the preparation of bone cement, it is particularly desirable to provide one of the components used to form the bone cement within a disposable mixing chamber. The mechanical complexity of the device of U.S. Pat. No. 5,348,391 tends to make the device non-disposable, and the meshing gears may not be compatible with the storage and shipment of a powdered component within the mixing chamber.

U.S. Pat. No. 4,671,263 to Draenert describes a pistol-shaped device for applying previously-mixed bone cement under pressure. The cement, which is mixed, for example, manually in a bowl external to the device, is introduced to a generally-cylindrical, sealable container forming a part of the device. This container is removably attached to a housing including a handle. A tapered distal end of the container is sealed by a removable closure cap. A pneumatically-operated sliding ejector extending initially within the housing engages a lamellar structure acting as a piston slidably mounted within the container, originally at a proximal end of the container. The cement mixture is prepressurized for about five minutes by means of a force exerted on the lamellar structure by the sliding ejector. During this process, gasses entrapped within the mixture escape past the lamallae of the lamellar structure along the inner surface of the container, while the lamallae prevent the escape of the cement mixture. The force exerted by the sliding ejector is then relieved, and the closure cap is removed, and the cement mixture is injected from the device by the repeated opening of a valve causing the pneumatic operation of the sliding ejector. In one version of the device, the container is additionally rotated about its axis.

While the device of U.S. Pat. No. 4,671,263 particularly addresses means for conditioning the previously-mixed bone cement before it is administered into the patient, and means for dispensing the mixture into the patient, the mixing of components of the cement remains a separate operation, to be carried out in separate apparatus. When the mixture is transferred from the mixing apparatus to the device described in this patent, it is exposed to the air, and hence to potential contamination and to polymerization problems which may occur with undue exposure to air. Furthermore, during this transfer of material, the air within the operating room is exposed to the mixture, and hence to the release of noxious and toxic gasses generated during the polymerization process. What is needed is apparatus providing an enclosure in which both mixing and application can occur.

While various devices from the prior art, including those including those of the patents described above, use a vacuum to prevent the entry into the ambient air of noxious gasses produced during the mixing process, none of these devices include means for indicating that an effective vacuum is being produced. The vacuum may be rendered ineffective by the failure of a pump or be the physical clogging of the apparatus at a number of points. This, what is needed is a mechanism providing a visual indication that the required vacuum is being produced.

U.S. Pat. No. 4,277,184 to Solomon describes an orthopedic implement providing a disposable, closed system in which bone cement is mixed and from which the mixed cement is dispensed. The closed system includes a chamber, a member reciprocable within the chamber, a mixing member operatively and axially receivable within the reciprocable member, and means for rotating the mixing member within the chamber. This means for rotating may be a pneumatic or electric drill. When the implement is to be used, the two components to be mixed are poured into the chamber, and the reciprocable member is inserted into the chamber with the mixing member extending through the reciprocable member. The mixing member is connected to the drill, being rotated thereby so that a pair of triangular vanes extending from the mixing member are rotated within the chamber. After mixing is complete, the mixing member is pulled outward so that its vanes are withdrawn into slots in the reciprocable member, a plug closing a lower opening to the chamber is removed, and the reciprocable member is pushed into the chamber, pushing the mixed cement outward therefrom, through the lower opening, and through a dispensing tube attached thereto.

While the device of U.S. Pat. No. 4,277,184 provides a closed chamber for mixing and dispensing bone cement, the containers in which the two components of the cement are supplied must be opened externally to the disposable implement and poured into the chamber. This part of the process exposes these components to possible contamination. What is needed is a means for providing these components within the implement and for opening packages within the implement as necessary before the mixing process is begun. Furthermore, since the triangular paddles sweep through only a small portion of the space within the chamber as the mixing member is rotated, and since there is no member scraping along the walls of the chamber during the mixing process, it is believed that mixing may not be optimally vigorous and through.

U.S. Pat. No. 4,463,875 to Tepic describes bone cement mixing apparatus in which the two components of the cement are vacuum-packaged in elongated flexible, fluid-tight compartments, which are abutted in a side-to-side arrangement to one another, and which are sealed together. These compartments are acted upon from each side by a dual piston arrangement including a hemispherically-shaped outer piston and a smaller inner piston. The inner piston may travel with the outer piston, or it may be extended into the adjacent compartment independently from the outer piston. The first piston movement collapses one of the compartments, rupturing the walls between the compartments, so that the components therein are mixed. Then, the two compartments are alternately collapsed and controlledly extended until the components therein form a homogenous cementitious mixture. Next, a nozzle is attached to one of the compartments in lieu of the other compartment, and the one compartment is collapsed to expel the mixture to the deposition site.

While the method of U.S. Pat. No. 4,463,875 provides the advantage of carrying out the mixing process before either of the components or the mixture is opened to the atmosphere, the apparatus required to carry out this method is complicated by the fact that two piston motions are required from each end of the compartments, which must therefor be placed centrally within the apparatus. Furthermore, no means is provided for establishing a vacuum before or after the mixing process, so noxious gasses resulting from the mixing process are released into the ambient air when the compartments are separated to install the nozzle. Also, there is no way to clear portions of the cement mixture remaining on the inner walls of the compartments following the mixing process. Also, providing the components together in a single, although divisible, package is complicated by the fact that they cannot be sterilized together, since the sterilization processes for the liquid and powder components are different and incompatible. That is, the liquid component cannot be exposed to the process presently used to sterilize the powder component, and the powder component cannot be exposed to the process presently used to sterilize the liquid component. Thus, what is needed is an apparatus holding both of the components of the cement, to which mixing motions are provided from a single end. Also, what is needed is a method for applying a vacuum to a chamber in which the components are mixed during the mixing process, and a means for scraping the inner wall of such a chamber to remove the mixture following the mixing process.

A method for advancing a shaft in a predetermined direction through a number of incremental manual motions of a crank is described in U.S Pat. No. 5,579,694 to Holung et al, in an application involving the attachment of a shutter to windows of varying width. This method, or a variation thereof, may be applied in a device using the movement of a piston engaged by an advancing shaft to dispense bone cement.

SUMMARY OF THE INVENTION

Thus, an object of the present invention is to provide an apparatus which can be readily used both for supplying and storing the components of a two-component bone cement, and for mixing these components in a sterile environment when the resulting mixture is needed.

Another object of this invention is to provide a mixing chamber in which the components of bone cement are thoroughly mixed, by moving structures including a flexible mixing and scraping structure moving along the wall of the mixing chamber.

Another object of this invention is to provide a method for thoroughly mixing the components of bone cement within a chamber by rotating a mixing rotor within the chamber.

Another object of this invention is to provide an apparatus in which bone cement components are mixed without exposing operating room personnel to direct contact with these materials or to contact with vapors released during the mixing process.

Another object of this invention to provide bone cement mixing apparatus including means giving a visual indication that a vacuum is being effectively applied within the mixing chamber.

Another object of this invention is to provide an apparatus in which the process of mixing bone cement may be carried to its conclusion without a need for operator intervention.

In accordance with one aspect of the invention, there is provided mixing apparatus including a container, a mixing structure, and a helical spring. The container includes a cylindrical outer wall extending along a cylinder axis. The mixing structure is mounted within the container to rotate about an axis of rotation coaxial with the cylinder axis, with the mixing structure including a first paddle extending longitudinally within the container. The helical spring has a first end attached to the mixing structure to turn therewith, with the helical spring being in sliding contact with an inner surface of the cylindrical outer wall.

In accordance with another aspect of the invention, there is provided apparatus for dispensing a liquid component of a mixture into a mixing chamber, with the liquid component being held within an ampule. The apparatus includes a supply section housing, an ampule holding structure, an ampule opening mechanism, and an intermediate cap. The ampule holding structure holds the ampule within the supply section housing. The ampule opening mechanism opens an ampule within the ampule holding structure to release the liquid component in the ampule. The intermediate cap includes an attachment structure for releasably attaching the mixing chamber to the cap and a dispensing hole for dispensing the liquid component into the mixing chamber.

In accordance with another aspect of the invention, there is provided apparatus for mixing a two-component cement, in which the apparatus includes a mixing housing, a mixing rotor, a drive base, and a liquid component supply section. The mixing rotor is mounted to rotate about an axis of rotation within the mixing housing. The drive base includes a clamping mechanism which engages and releases a first end of the mixing housing, and a rotating drive mechanism which engages and releases the mixing rotor. The liquid component supply section includes a supply section housing, an ampule holding structure for holding an ampule within the supply section housing, an ampule opening mechanism for opening the ampule within the ampule holding structure, and an intermediate cap including attachment means for releasably attaching a second end of the mixing housing (opposite the first end of the mixing housing), and a dispensing hole for dispensing the liquid component into the mixing housing.

In accordance with another aspect of the invention, there is provided dispensing apparatus including a housing, a dispensing tube, a piston, a removable plug, a hollow piston feeding shaft, a dispensing mechanism, and a pushrod. The housing includes a hollow cylindrical portion, with a housing end cap portion extending across a distal end of the hollow cylindrical portion, and with a central dispensing hole within the housing end cap. The piston is movable within the hollow cylindrical portion, and in contact with an internal surface of this portion, toward the distal end of the housing. The removable plug is centrally located within the piston, being disposed toward the dispensing tube. The dispensing mechanism includes a holder in which the housing is held, and a shaft feeding mechanism for moving the hollow piston feeding shaft into the hollow cylindrical portion of the housing, toward the distal end of this portion, with the housing within the holder. The pushrod can be moved within and along the hollow piston feeding shaft to move the removable plug within and along the dispensing tube.

BRIEF DESCRIPTION OF THE DRAWINGS

FIG. 4 is a longitudinal cross-sectional view of the mixing section in the apparatus of FIG. 1, assembled in a configuration used to dispense the bone cement therefrom;

FIG. 5 is a schematic view of circuits used with the motorized drive base of FIG. 1 to rotationally drive the mixing rotor therein;

FIG. 6 is a longitudinal cross-sectional view of a manually-operated drive base alternately used a mixing rotor of the apparatus of FIG. 1;

FIG. 7 is a longitudinal cross-sectional view of a funnel inserted to add a liquid component to the mixing section of the apparatus of FIG. 1.

FIG. 8 is a longitudinal cross-sectional view of a vacuum-retaining cap alternately used with the mixing section of the apparatus of FIG. 1;

FIG. 9. is a longitudinal cross-sectional view of an alternative vacuum-retaining cap alternately used with the mixing section of the apparatus of FIG. 1 in the absence of the motorized drive base of FIG. 1 and of the manually-operated drive base of FIG. 6.

DETAILED DESCRIPTION

Figures 1, 2, 3:
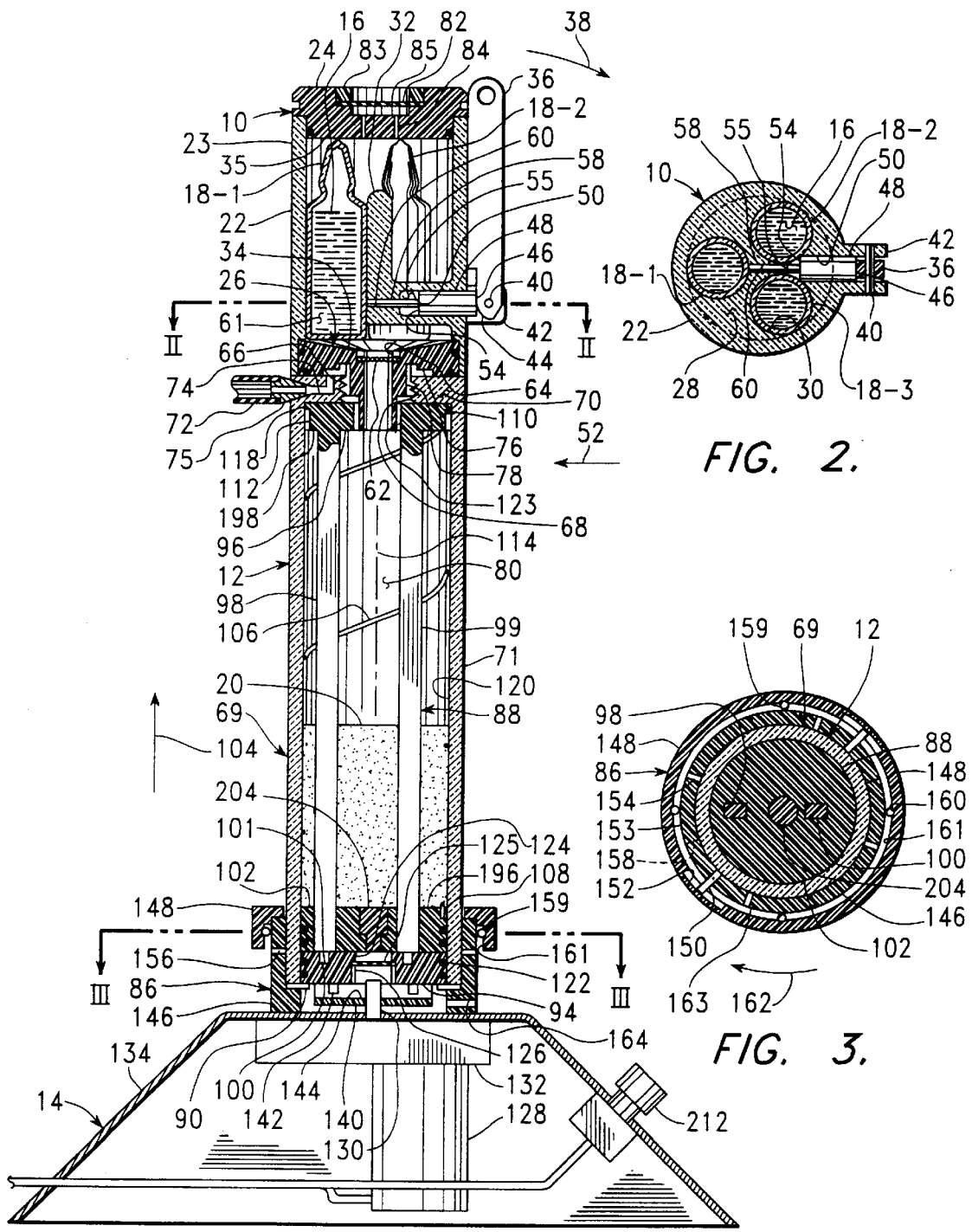
FIG. 1 is a longitudinal cross-sectional view of apparatus built in accordance with a preferred embodiment of the present invention, assembled in a configuration for mixing the two components of bone cement.
FIG. 2 is a transverse cross-sectional view of the apparatus of FIG. 1, taken as indicated by section lines II—II in FIG. 1 to show the elements used to hold and open ampules within a first-component supply section of this apparatus.
FIG. 3 is a transverse cross-sectional view of the apparatus of FIG. 1, taken as indicated by section lines III—III in FIG. 1 to show a mixing rotor within this apparatus and to show a clamping mechanism holding a motorized drive base to the remainder to the apparatus of FIG. 1.

FIG. 1 is a longitudinal cross-sectional view of apparatus built in accordance with a preferred embodiment of the present invention, assembled in a configuration for mixing the two components of bone cement. The main sections of this apparatus are a first component supply section, generally indicated as 10, a mixing section, generally indicated as 12, and a motorized drive base, generally indicated as 14.

The liquid component 16 of the bone cement is supplied in one or more sealed glass ampules 18 within the first component supply section 10. In the exemplary version of FIG. 1, the supply section 10 includes three ampules 18, which are individually referenced and referred to herein as ampules 18-1, 18-2, 18-3. The supply section 10 is made available in different versions, according to the number of ampules, which are employed depending on the quantity of bone cement needed for a particular operation.

The powder component 20 of the bone cement is preferably supplied within the mixing section 12. The mixing section 12 is preferably also supplied in different versions, containing differing amounts of the powder component 20, in correspondence with the number of ampules 18 within an associated first component supply section 10, in attachment with which the mixing section is preferably supplied.

FIG. 2 is a transverse cross-sectional view of the apparatus of FIG. 1, being taken as indicated by section lines II—II in FIG. 1 to show the elements used to hold and open the ampules 18-1, 18-2, and 18-3.

Referring to FIGS. 1 and 2, the first component supply section 10 includes a housing 22, an upper end cap 24, and an intermediate supply section cap 26. The housing 22 includes a cylindrical outer wall portion 23 and an ampule supporting partition portion 28. One to three ampule(s) 18 are held within the three apertures 30 provided within the ampule supporting partition 28 for this purpose. The ampules 18 are also arranged around a post 32 extending upward as a part of supporting partition 28. Furthermore, the ampules 18 extend between a truncoconical upper surface 34 of the intermediate supply section cap 26 and a flat lower surface 35 of upper end cap 24.

The process of mixing the components 16,20 to make bone cement begins with the opening of ampule(s) 18 by manually rotating an external lever 36 downward, in the direction of arrow 38. This external lever 36 is mounted to rotate about a pin 40 extending through a lever pivot tabs 42, which extend outward as portions of the housing 22. The downward rotation of external lever 36 brings a camming surface 44 of the lever 36 into contact with an outer face 46 of a cylindrical slider 48, which slides in a hole 50 of the ampule supporting partition 28. Further downward rotation of external lever 36 causes the camming surface 44 to move the slider 48 inward, in the direction of arrow 52, so that the edge of inner face 54 of the slider 48 moves through openings 55 at the intersection of the hole 50, within which the slider 48 operates, and two of the apertures 30 within supporting partition 28 with the hole 50. This movement of the slider 48 opens adjacent ampules 18-2, 18-3. A pin 58 forming a portion of slider 48 extends further into supporting partition 28 through a hole 60 therein, additionally opening ampule 18-1 with movement of the slider in the direction of arrow 52. Thus, as external lever 36 is rotated downward, in the direction of arrow 38, each of the ampules 18 within the first component supply section 10 is opened.

The walls of each ampule 18 may be composed of a breakable glass or plastic material, which is cracked and broken open by the movement of the slider 48. Alternately, each ampule 18 may be composed of a relatively tough plastic material, with ampule 18-1 being punctured by the pin 58, while the adjacent ampules 18-2, 18-3 are cut open by the movement of the slider 48.

After the ampules 18 are broken or cut, their liquid contents 16 flow downward to fill the lower portion of a chamber 61 within the first component supply section 10 above an intermediate filter 62, which is held in place within the cap 26 by means of an annular retainer 64. The filter 62 prevents the entry of residue from the walls of broken or cut ampules 18, such as glass or plastic shards, into the mixing section 12.

The mixing process is carried out in mixing section 12 with the upper supply section 10 and the mixing section 12 tightly connected by means of an externally-threaded section 66 extending downward as a part of the supply section intermediate cap 26 in engagement with an internally-threaded hole 68 of the housing 69 of mixing section 12. The housing 69 includes an intermediate cap portion 70 and a cylindrical cover portion 71.

The mixing process is also carried out under conditions of a vacuum, which is applied through a hose 72 fastened onto a vacuum port 74, by means of a releasable coupling 75, so that the hose 72 extends outward from the mixing section intermediate cap portion 70. The vacuum port 74 also extends upward to an annular groove 76, which extends around the externally threaded section 66 in the supply section intermediate cap 26. This annular groove 76 also extends above a number of slots 78, which in turn extend downward through the eternally-threaded section 66 into the chamber 80 within mixing section 12. Thus, when a vacuum is drawn through the hose 72, air and volatile products of chemical reactions occurring during mixing flow upward, through the slots 78, around through annular groove 76, and outward through the port 74 and hose 72.

The application of a vacuum to the chamber 80 within mixing section 12 also facilitates the flow of the liquid cement component 16 through the filter 62 into this chamber 80, so that mixing can occur. In a preferred mode of operation, the ampules 18 are opened before the application of a vacuum through the hose 72, so that pressure differential available across the liquid contents of the lower portion of the chamber 61 is maximized. This pressure differential, formed as the mixing section chamber 80 is evacuated with atmospheric pressure being retained in the supply section chamber 61, causes the rapid flow of these liquid contents through the filter 62, while residue from the opened ampules 18 remains above the filter 62, or imbedded therein. A flexible vacuum indicator disk 82, retained in place within upper end cap 36 by an annular retaining collar 83, provides a visual indication, by depression, of a vacuum within the chamber 61. This indicator disk 82 is be composed, for example, of an elastomeric material. The depression of the vacuum indicator disk 82 is caused by the application of the vacuum to the underside of this disk 82 through a number of holes 84 within the upper cap 24. Thus, the depression of the vacuum indicator disk 82 indicates that the vacuum through hose 72 is operational, and that the liquid contents from the ampules 18 have been sucked through the filter 62.

In a preferred version of the present invention, the vacuum indicator disk 82 is composed of a material which is both suitably deflectable and translucent. A distinctive color or pattern is applied to the surface 85 underlying the disk 82, with this color or pattern being easily discerned only when the indicator disk 82 is pulled down by an underlying vacuum so that a central portion of this disk lies against the surface 85. The disk 82 is pulled down in this way when a level of vacuum suitable for the mixing process, such as 22 inches of mercury, is applied from below.

FIG. 3 is a transverse cross-sectional view of the apparatus of FIG. 1, taken as indicated by section lines III—III in FIG. 1 to show the structure of mixing section 12 and of a clamping mechanism 86 holding the mixing section 12 in place on motorized drive base 14.

Referring to FIGS. 1 and 3, the mixing section 12 includes the stationary housing 69, the powder component 20 to be mixed into cement, and a mixing rotor 88. The mixing section intermediate cap 70, which forms a portion of the stationary housing 69, has been described above, relative to its functions of releasably connecting the mixing section 12 with the first component supply section 10 and of connecting a vacuum established through hose 72 with the chamber 80 within mixing section 12. The lower flange 90, which is adhesively joined to the lower end of cylindrical cover portion 71, holds the mixing rotor 88 in place within the stationary container 86.

The mixing rotor 88 includes a lower end cap 94, an upper end cap portion 96 and a pair of paddles 98, 99 extending downward from the upper end cap portion 96 to be fastened by an adhesive to the lower end cap 94, with pin portions 100 of the paddles 98, 99 fitting into mating holes 101 within the lower end cap 94 . The mixing rotor 88 also includes a piston 102, mounted to slide along the paddles 98, 99 in the longitudinal direction indicated by arrow 104, and a helical mixing wire spring 106 having a first end 108 fastened to the piston 102 and a second end 110 extending within a spring receiving groove 112 in the upper end cap portion 96. The mixing rotor 88 is mounted to rotate about an axis of rotation 114, collinear with the longitudinal axis of the cylindrical cover portion 71, by means of the engagement of a cylindrical outer surface 118 of upper end cap 96 with the inner surface 120 of the cylindrical cover portion 71, and also by means of the engagement of a pair of circular sealing rings 122 of the lower end cap 94 with this inner surface 120. (The longitudinal axis of the cylindrical cover portion 71 is herein understood to be a line connecting the centers of the circular spaces within the inner surface 120 at each end thereof.) The upper end cap portion 96 includes a hole 123 through which the liquid component of the cement enters the chamber 80 within the mixing section 12, and through which mixed cement is subsequently dispensed, in a manner which will be described in reference to FIG. 4.

The lower end cap 94 includes an aperture 124, which is needed to provide access to the piston 102, so that the mixed cement can be driven out of the chamber 80 in a manner described below in reference to FIG. 4. In order to maintain a sealed, sterile environment within the chamber 80 before and during the mixing process, the aperture 124 is sealed by means of an elastomeric diaphragm 125, which is held in place by a retaining ring 126.

The mixing rotor 88 is driven in rotation about its axis of rotation 114 by means of a motor 128 in the motorized drive base 14, to which the mixing section 12 is releasably attached by means of a base clamping mechanism 86. Within the drive base 14, the motor 128 drives a shaft 130 in rotation through a speed-reducing gear box 132. External to the housing 134 of the drive base 14, a drive disk 140 turns with the shaft 130 engaging the mixing rotor 88 through a pair of drive pins 142 extending downward, as portions of the lower end cap 94, into a transverse drive slot 144 within the mixing rotor 88.

After the liquid component 16, is released from the first component supply section 10 into the mixing section 12, the rotation of mixing rotor 88 thoroughly mixes the two components 16, 20 of the cement. The outer paddle 98 and inner paddle 99 are arranged so that the sweep through radially differing paths within the resulting mixture (not shown). The helical mixing wire spring 106 serves a particularly important function, as it sweeps material off the inner surface 120 of the cylindrical cover portion 71 with rotation of the mixing rotor 88. The flexible nature of the helical mixing wire spring 106 allows sliding contact with the inner surface 120 to occur along the length of the spring without preventing rotation of the mixing rotor 88 by jamming against the inner surface 120.

In this way, a particular advantage of the present invention is gained relative to those devices in the prior art, such as the devices of U.S. Pat. Nos. 4,185,072, 4,277,184, and 5,348,391, which include rigid mixing rotors, lacking flexible components to be dragged along the wall of the vessel in which mixing occurs. This advantage is especially important due to a need to mix all of the liquid component with all of the powder component. This need arises from the potential for adverse reactions if unmixed portions of the liquid component are released into the patient and from the potential for weakened areas in the cement if unmixed portions or the powder component are included in pockets within the hardened cement.

The clamping mechanism 86 includes a receiving ring 146 attached to the motorized drive base 14 and a locking ring 148 mounted to pivot through a limited angle on the receiving ring 146. A pair of mounting pins 150 extend outward from the receiving ring 146 into a corresponding pair of slots 152 within the locking ring 148, holding the locking ring 148 on the receiving ring 146 in place on the receiving ring 146 and restricting the pivoting motion of the locking ring 148 to an angle permitted by the length of the slots 152. The receiving ring 146 includes four circumferentially extending cantilever arms 153, each of which is separated from adjacent portions of the receiving ring 146 by a vertical slot 154 and a horizontal slot 156 extending to a slot end 158. Each cantilever arm 153 is in sliding and rolling contact with a ball 159 held within a depression 160 in an inner surface 161 of the locking ring 148. The cantilever arms 153 are configured so that, when the locking ring 148 is held at the extreme of its motion in the direction of arrow 162, with each of the balls 159 held near the end 163 of a corresponding cantilever arm 153, the mixing section 12 fits loosely within the clamping mechanism 86. As the locking ring 148 is turned in the direction opposite that of arrow 162, the balls 159 are slid and rotated along the cantilever arms 153, increasing the engagement between the balls 159 and the arms 153, so that these arms 153 are held against the mixing section 12 within the clamping mechanism 86. Each cantilever arm 153 is tapered so that it is thinnest at its end 163. The receiving ring 146 includes a hole 164 which allows the entry or exit of air, so that a build-up of pressure within the ring 146 does not resist the insertion therein of the lower portion of the mixing station 12, and so that a resulting vacuum does not resist the removal therefrom of the lower portion of the mixing station 12.

Thus, before the mixing process is started, the mixing section 12 is placed within the clamping mechanism 86, with the locking ring 148 turned in the unlocking direction of arrow 162. Preferably, this placement is made so that the drive pins 142 extending downward from the lower end cap 94 within the mixing rotor 88 fit into the transverse slot 144 of drive disk 140. Otherwise, the mixing section 12 is manually rotated through incremental motions until it can be moved downward, indicating the proper alignment of the pins 142 within the slot 144. When the proper engagement between the pins 142 and the slot 144 is achieved, the locking ring 148 is rotated in the locking direction opposite arrow 162.

When the mixing process is complete, the mixing section 12 is removed from the motorized base 14 by disengaging the base clamping mechanism 86, as described above, by rotating locking ring 148 in the unlocking direction of arrow 162, and by lifting the mixing section 12 upward, out of the clamping mechanism 86. The mixing section 12 is also disengaged from the first component supply section 10 by unscrewing the connection between externally-threaded section 66 of the supply section intermediate cap 26 and the internally threaded hole 68 of the mixing section housing 69.

FIG. 4 is a longitudinal cross-sectional view of the mixing section 12 from the apparatus of FIG. 1, in a configuration used to dispense the just-mixed bone cement 165. In the example of FIG. 4, most of the bone cement has been dispensed therefrom. After the removal of the mixing section 12 from the motorized base 14 and from the first component supply section 10, a dispensing tube 166 is attached to the mixing section 12, with an externally-threaded end 168 of the discharge tube 166 engaging the internally threaded hole 68 of mixing section housing 69. The mixing section 12 is also placed within a dispensing gun, generally indicated as 170.

The dispensing gun 170 includes an open holder 172 in which the mixing section 12 is placed, with this open holder 172 comprising several support rods 174, a proximal flange 176, and a distal flange 178. The distal flange 178 includes a slot 179 which is upwardly open to allow the movement therethrough of discharge tube 166. The proximal flange 176 is attached to a feed mechanism 180, which incrementally feeds a piston-driving tube 182 in the feed direction indicated by arrow 184, as a lever 186 is manually and repeatedly pivoted in the direction indicated by arrow 188. The operation of the feed mechanism 180 is understood by those familiar with the art of such devices, being similar to the mechanism of a caulking gun. A mechanism for feeding a shaft under manual control, from another art, is also shown in U.S. Pat. No. 5,579,604 to Holung, et al.

The piston-driving tube 182 is fastened to an annular piston-driving tip 190, which engages the piston 102. A first portion of this motion of tube 182 causes the tip 190 to rupture the elastomeric diaphragm seal 125. As the piston 102 is moved in the direction of arrow 184 in contact with the piston-driving tip 190, the mixed cement 165 is forced down the dispensing tube 166 to be expelled at its distal opening 194. When this motion is completed, as shown in FIG. 5, the distal surface 196 of piston 102 is brought into contact with the inner proximal surface 198 of housing 69, with the cement within the mixing section chamber 80 (shown in FIG. 1) having been pushed into the dispensing tube 166. During this motion of the piston 102, a reverse flow of mixed cement past the piston 102 is prevented by a pair of flexible seals 200 extending around the piston 102 in sliding contact with the inner cylindrical surface 120 of housing 69. Also during this movement of the piston 102, the helical spring 106 is collapsed into the spring receiving groove 112 in the upper end cap 25. In this way, the spring 106, which is held in contact with the inner surface 120 of the cylindrical cover 92 as advantage is taken of the resilience of the spring, sweeps mixed cement from the inner surface 120 with the movement of piston 102.

As shown in FIG. 4, the movement of piston 102 leaves the dispensing tube 166 full of mixed cement 165. To facilitate dispensing this material, a pushrod 202 is inserted through the hole 203 within the piston-driving tube 182, in the direction of arrow 184. With continued manually exerted force, this pushrod 202 then pushes a plug 204 within the piston 102 in the direction of arrow 184 through the dispensing tube 166. This motion dispenses the mixed cement 165 remaining in the dispensing tube 166 through its distal opening 194, with the plug 204 clearing cement from the interior surface 206 of the tube 166.

Thus, the various features of the present invention, as described above, clear virtually all of the mixed cement from both the chamber 80 within the mixing section 12, and from the dispensing tube 166, through the opening 194 at the distal end of the dispensing tube 166.

FIG. 5 is a schematic view of circuits used to drive the apparatus of FIG. 1 during the mixing process in accordance with a preferred version of the present invention. Circuits within a control box 210 are used to operate the motor 128 within the motorized drive base 14, in response to the depression of a switch mechanism 212 also within the drive base 14. (These elements of the drive base 14 are also shown in FIG. 1).

Referring to FIGS. 1 and 5, the depression of the switch 212 causes an electronic counter 214 to start providing output pulses to motor drive logic 216 and to an audio data addressing circuit 218. The motor 128 is preferably driven to cause the mixing rotor 88 to be rotated at a speed of 1 to 2 revolutions per second in alternating directions. For example, the mixing rotor 88 is driven for five seconds in alternating directions, with an idle time of one-half second, during which no driving voltage is applied to the motor 128, occurring between the application of voltages having different polarities. Thus, the counter 214 provides a first signal every half-second to time the idle period and a second signal every five seconds to time the application of voltages of differing polarities. The motor 128 is a permanent magnet type rotating in different directions according to the polarity of a direct current driving signal applied across its armature. To drive the motor 128 in a first direction, the motor drive logic 216 applies a voltage to the motor through a first driver 220. To drive the motor 128 opposite the first direction, the motor drive logic 216 applies an opposite voltage to the motor through a second driver 222.

Audio data storage 224 includes digitally recorded audio information in the form of messages which can be addressed individually. Each such message indicates the length of time which has elapsed since the starting of counter 214 by the depression of switch 212. For example, the counter 214 provides a signal pulse to audio data addressing circuit 218 every 30 seconds, with the first message being "thirty seconds," the second message being "one minute," and the third signal being "ninety seconds." As the signal pulses from counter 214 are received, the addressing circuit sequentially addresses these stored messages within the storage unit 224. The resulting messages are fed through a signal conditioning and amplification circuit 226 to a speaker 228. In this way, audible information is provided to indicate the length of time that mixing has occurred. Depending particularly on the desires of an individual surgeon concerning the consistency of the bone cement to be dispensed in an individual operation, the mixing process generally takes from 60 to 90 seconds.

The pushbutton switch 212 is arranged to start the mixing process when it is depressed for a first time and to stop the mixing process when it is depressed for a second time. This can be done with a commercially-available "push-push" switch having a button that remains depressed, with electrical contacts held together, after it is depressed for the first time. With the second depression, the button of such a switch is released from depression, and the electrical contacts are separated. Alternately, a pushbutton switch without the mechanism providing the "push-push" function may be used, with the sustained operation of the mixing apparatus being sustained by setting an electronic flip-flop, which is subsequently reset by the second depression of the pushbutton switch. In either case, depressing the pushbutton switch 212 the first time turns on the mixing process, starting the electronic counter 214. Depressing the pushbutton switch 212 the second time stops the mixing process, stopping and resetting the electronic counter 214. If the pushbutton switch is not depressed, the mixing operation is automatically stopped by an output of the counter 214 to the motor drive logic 216 after a predetermined maximum running time, such as ninety seconds.

FIG. 6 is a longitudinal, vertical cross-sectional view of a manually-operated drive base, generally indicated as 230, in which a manually-rotated crank 232 replaces the drive motor 126 of the motorized drive base 14 (shown in FIG. 1). The manually-operated drive base 230 includes the clamping mechanism 86, which has been previously described in reference to FIGS. 1 and 3 as a portion of the motorized drive base 14, for removably clamping the mixing section 12 in place. Like reference numerals are used to describe the features of this mechanism 86 in reference to FIG. 6. The manually-operated drive base 230 also includes the drive disk 140 which is used, as previously described in reference to FIG. 1, to form a mechanical connection imparting rotary motion to the mixing rotor 88 within the mixing section 12. The drive disk 140 is attached to a drive shaft 232, which is mounted to rotate within a pair of bearings 234, being rotationally driven by a drive belt 236 engaging a pulley 238 also attached to the drive shaft 232. The drive belt 236 is in turn driven by a manually-driven crank 240 through a crank shaft 242 rotating in a pair of bearings 244 with a pulley 246. These elements are surrounded by a housing 248. A rotatable knob 250 is attached to the other end of the crank 240 to facilitate its manual operation.

Referring to FIGS. 1 and 6, before the mixing process is begun with the manually-operated drive base 230, the mixing section 12 is placed in the clamping mechanism 86 of this base 230, with the locking ring 148 rotated in the unlocking direction of arrow 162 (shown in FIG. 3). The mixing section 12 is rotated as necessary and/or the crank 240 is rotated incrementally, in order to bring the drive pins 142 extending downward from the mixing section 12 into alignment with the transverse drive slot 144 of the drive wheel 140. When this alignment is attained, the mixing section 12 is moved downward into the clamping mechanism 86. Next, the mixing section 12 is locked in place within the clamping mechanism 86 by rotating the locking ring 148 opposite the unlocking direction of arrow 162. With this movement of the locking ring 148, the four balls 159 moving with the locking ring 148 urge corresponding cantilever arms 153, forming portions of the receiving ring 146 of the clamping mechanism 86, inward to grip the mixing section 12 during the subsequent mixing process. As the mixing process is applied through the manually-operated drive base 230 by manually rotating the crank 240. To facilitate mixing, the crank may be rotated for a predetermined number of revolutions in alternating opposite directions. After the mixing process is completed, the mixing section 12 is released by rotating the locking ring 148 in the direction of arrow 162, and by lifting the section 12 out of the receiving ring 146.

FIG. 7 is a longitudinal cross-sectional view of a funnel 251 in place to fill the mixing section 12 with a liquid component (not shown). The preceding description has considered the use of mixing section 12 with the first component supply section 10 and with either the motorized drive base 14 or the manually-operated drive base 230. The mixing section 12 may also be used in manner of FIG. 7, and in the absence of the first component supply section, with the liquid component of the cement being poured into the mixing section 12 through the threaded hole 68 in the top of the mixing section housing 69 and through the hole 123 in upper end cap portion 96. The tip portion 252 of funnel 251 is preferably long enough to extend through both of these holes 68, 123. The liquid component poured into the funnel 251 may be derived, for example, from an opened ampule. The powder component of the cement is preferably supplied within the chamber 80 of the mixing section 12. Sterile conditions within the mixing section 12 must be maintained by sealing the hole 123 with an adhesive label which is removed before the section is used.

FIG. 8 is a longitudinal cross-sectional view of a vacuum-retaining cap 254, which is used to provide the vacuum mixing capabilities, described above in reference to FIG. 1, in an absence of the first-component supply section 10.

Referring to FIGS. 1 and 8, the vacuum-retaining cap 254 provides various features previously described as parts of the first component supply section 10, for attachment to the mixing section 12, for achieving and retaining a vacuum within the chamber 80 of the mixing section during the mixing process, and for providing a visual indication that a vacuum has been retained in the chamber 80. In this description of the vacuum-retaining cap 254, like reference numerals with similar features of the mixing section 12 are used.

The vacuum-retaining cap 254 is configured to be attached atop the mixing section 12 in place of the first-component supply section 10, with an externally-threaded section 66 engaging the internally-threaded hole 68 within housing 69 of the mixing section 12. As the cap 254 is attached to the top of the mixing section 12, a sealing ring 256 forms a pressure-tight seal along the top surface of the housing 69, and an annular groove 76 is connected with the vacuum port 74 within the housing 69. A number of slots 78 in the threaded section 66 extend between the annular groove 76 and chamber 80 within the mixing section 12. Thus, when a vacuum is applied to the vacuum port 74 of the housing 69 through the hose 72, gasses from the chamber 80 flow upward through the slots 78, around through the groove 76, and outward through the port 74.

The cap 254 also includes a number of holes 84, extending upward from the chamber 80 with mixing section 12 attached to the cap 254, to a flexible vacuum indicating disk 82 held in place by an annular retainer 83. When a vacuum is drawn within the chamber 80, a visual indication is provided by the depression of the vacuum indicating disk 82. As previously described in reference to FIG. 1, the indicating disk 82 is preferably composed of a translucent material which reveals a color or pattern on the underlying surface 85 only when the central portion of the disk 82 is held against this surface 85 by a pressure differential across the disk 82.

FIG. 9 is a longitudinal cross-sectional view of an alternative vacuum retaining cap 260, having the features described above in reference to the vacuum retaining cap 254 of FIG. 8 for achieving and retaining a vacuum in the chamber 80 of an attached mixing section 12, and additionally having a manually-operated crank 262 applying rotary motion to the mixing rotor 88 within the mixing section 12. The preceding discussion has described the use of mixing section 12 with either the motorized mixing base 14 or the manually-operated drive base 252. Thus, the alternative cap 260 may be used without either of the bases 14, 252.

Referring to FIGS. 1 and 9, the alternative cap 260 includes an externally threaded section 66 for attachment to a mixing section 12, along with an annular groove 76 and slots 78, which are used as described above in reference to FIGS. 1 and 7, so that a vacuum is achieved and retained within the chamber 80 of the attached mixing section 12 when a vacuum hose 72 is attached to the vacuum port 74 thereof. The alternative cap 260 also includes a central hole 264 extending therethrough, in which the crank 252 is rotatably mounted by means of a downward-extending tubular section 266. Below the tubular section 266, a driving section 268 of the crank 262 extends within the hole 123 of the mixing rotor 88 in the mixing section 12. In this example, both the hole 123 and the outer surface of driving section 268 are square, so that the engagement of the hole 123 with the driving section 268 causes the mixing rotor 88 to turn as the crank 262 is rotated within the central hole 264. The crank 262 also includes a central hole 270 extending upward from the chamber 80 of an attached mixing section 12 to a number of smaller holes 84 extending to a surface 85 underlying a flexible vacuum indicating disk 82 held in place by an annular retainer 83. When a vacuum is drawn within the chamber 80, a visual indication is provided by the depression of the vacuum indicating disk 82. Again, the disk 82 is preferably translucent, so that a color or pattern on the underlying surface 85 is clearly visible only when the pressure differential across the disk 82 is sufficient to hold a central portion of the disk 82 against the surface 85. A handle 272 is rotatably mounted to an end of the crank 262 to facilitate manually operating the crank 262.

The crank 262 may be held in rotational engagement with the cap 260, by means of a clip (not shown) permitting rotation of the crank 262 while preventing its removal from the cap 260. With such an arrangement, the components to be mixed must be poured into the chamber 80 within the mixing section 12 before cap 260 is installed onto the section 12.

Alternately, the crank 262 may be easily removed from the cap 260. With such an arrangement, the cap 260 may be installed, without the crank 262, on the mixing section 12, so that the components to be mixed can be poured into the chamber 80 through the central hole 264 before the crank 262 is installed to begin the mixing process. A funnel is used to prevent contamination of the holes 264 and 123.

Figure 10:
FIG. 10 is a longitudinal cross-sectional view of an alternate piston which can be used in the apparatus of FIG. 1.

FIG. 10 is a longitudinal cross-sectional view of an alternative piston 276 having an annular groove 278 into which a helical spring 280 collapses as the piston 276 is driven toward the intermediate cap portion 70 (shown in FIG. 1). This annular groove 278 can be used to provide a space for the collapsed helical spring either in place of the annular groove 112 of upper end cap 96, or both of the grooves 112,278 may be used together to provide space for the collapsing helical spring.

Figure 11:
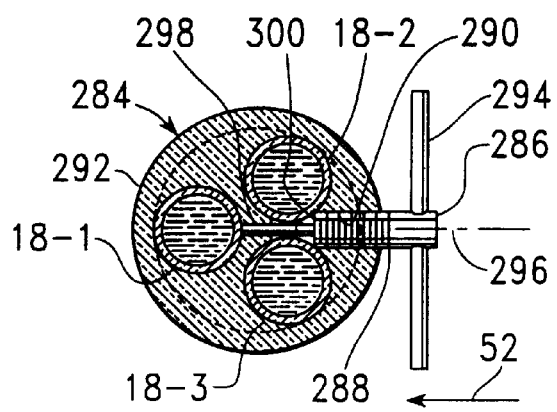
FIG. 11 is a transverse cross-sectional view of alternative apparatus for holding and opening ampules to supply a liquid component to the mixing section in the apparatus of FIG. 1.

FIG. 11 is a transverse cross-sectional view of an alternative first-component supply section 284, which can be used in place of the first-component supply section 10 described above in reference to FIGS. 1 and 2. As previously described, in the first-component supply section 10, the ampule-opening motion is provided by the sliding motion of a slider 48, which is in turn caused by rotating a lever 36 downward to provide a cam action with a lever surface 44 operating against an end 46 of the slider 48. On the other hand, in the alternative first-component supply section 284, the ampule-opening motion occurs as a screw 286, having external threads 288 in engagement with internal threads in a hole 290 of the housing 292 is driven inward, in the direction of arrow 52 by means of the rotation of a crank 294 about the axis of rotation 296 of the screw 286. The opening of an ampule 18-1 occurs as an inward-extending pin portion 298 of the screw 286 is driven against this ampule 18-1. The opening of ampules 18-2 and 18-3 occurs as an inward-directed face 300 of the screw 286 is driven against these ampules 18-2 and 18-3. Other features of the alternate first-component supply station 284 are like those of the first-component supply section 10, which have been described in detail in reference to FIGS. 1 and 2.

Figure 12:
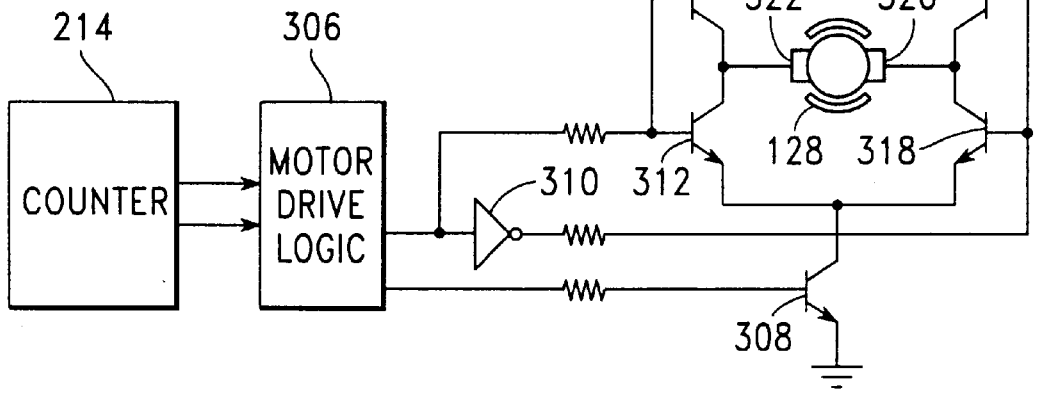
FIG. 12 is a schematic view of a circuit providing operation in alternate directions for the motor in the drive base of the apparatus of FIG. 1.

FIG. 12 is a schematic view of an alternative motor drive circuit 304, which is used to drive the motor 128 in alternately reversed directions. In the circuit described above in reference to FIG. 5, the motor 128 is driven by independently operated driver circuits 220, 222 applying voltages of opposite polarities to a single motor input. In the alternative motor drive circuit 304, both of the motor inputs are switched, with a single input voltage being applied to travel through the motor 126 in alternately opposite directions.

In the example of FIG. 12, motor drive logic 306 receives inputs from a counter 214, which operates generally as described above in reference to FIG. 5. Thus, a first counter output determines the time that the motor 128 is turned of between operation in reversed directions. A second counter output, which occurs at a multiple of the first counter output, determines the time that the motor 128 is left on for rotation in each direction. A third counter output indicates that the counter has been stopped, either by the depression of the pushbutton 212 (shown in FIGS. 1 and 5) or by reaching a terminal count determined to correspond to a maximum mixing time. The motor drive logic 306 in turn produces an output signal driving the base of an enabling transistor 308 whenever the motor is to be turned on to operate in either direction. Thus, this signal driving the enabling transistor 308 is turned on when operation of the motor with the counter 214 is begun and is turned off whenever operation of the motor is ended. Also, this signal is turned off for a predetermined time between operation of the motor 128 in opposite directions.

The motor drive logic 306 also produces a signal used as an input to an invertor circuit 310 and as an input to the bases of a first direction-switching transistor 312 and of a second direction-switching transistor 314. The output of the invertor circuit 310 is provided as an input to the bases of a third direction-switching transistor 316 and a fourth direction-switching transistor 318. When the signal from motor drive logic to the invertor 310 is present, the npn transistor 312 is turned on, while the pnp transistor 314 is turned off. Furthermore, the lack of an output signal from invertor 310 causes the pnp transistor 316 to be turned on, while the npn transistor 318 is turned off. Under these conditions, assuming the enabling transistor 308 is also turned on, the current flows from the +12V supply terminal through the pnp transistor 316 to a first terminal 320 of the motor 128, through the motor 128 between the first terminal 320 and a second terminal 322, through the npn transistor 312, and to ground through the enabling transistor 308.

On the other hand, when the signal from motor drive logic 306 driving invertor 310 is off, the npn transistor 314 is turned on, while the pnp transistor 312 is off. This condition turns on the output of invertor 310 to turn on, so that the pnp transistor 316 is turned off while the npn transistor 318 is turned on. Under these conditions, assuming that the enabling transistor 308 is turned on, current flows from the +12V supply terminal through the npn transistor 314 to the second motor terminal 322, through the motor 128 to the first motor terminal 320, and through the pnp transistor 318 and the enabling transistor 308 to electrical ground. Thus, alternating the level of the output signal driving the invertor 310 causes the alternation of the direction current through the motor 122, and hence the direction in which this motor 128 is driven.

Figure 13:
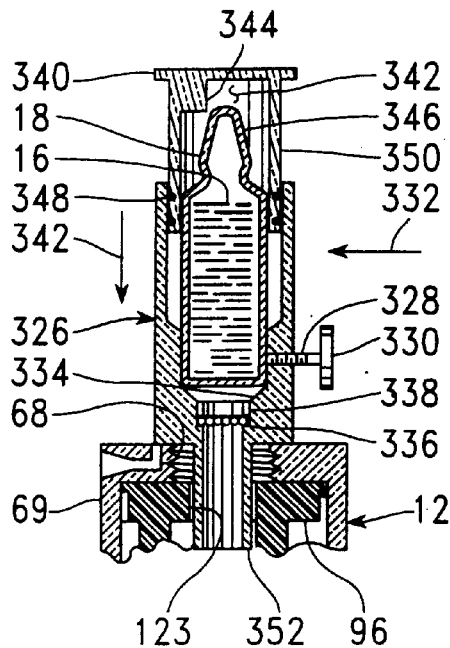
FIG. 13 is a longitudinal cross-sectional view of alternative apparatus for holding and opening a single ampule to supply a liquid component to the mixing section in the apparatus of FIG. 1.

FIG. 13 is a longitudinal cross-sectional view of a second alternative first component supply section 326, which is used to supply the liquid contents 16 from a single ampule 18 into the mixing section 12, which has been described in reference to FIGS. 1 and 3. This supply section 326 includes a single ampule 18, which is opened by manually turning a screw 328 with an attached wheel 330 so that the screw moves inward, in the direction of arrow 332. After the ampule 18 is opened, the liquid 16 runs down a truncoconical section 334 to a filter 336, which retains residue, such as glass or plastic shards from the opened ampule 18. The filter 336 is held in place by an annular retainer 338.

While this supply section 326 is being used, a vacuum is not applied within the mixing section 12, so it is desirable to apply pressure to the liquid 16, forcing it through the filter 336. Such pressure is applied by manually depressing a plunger 340 in the direction of arrow 342. The resulting downward movement of the plunger 340 compresses the air within a chamber 342 within the plunger 340 and moves an eccentric ampule-opening portion 344 of the plunger 340 into contact with the upper portion 346 of the ampule 18, so that this upper portion 346 is broken off. Sealing rings 348 prevent the outward flow of air and liquid under pressure around the cylindrical portion 350 of the plunger 340, while the liquid is forced through the filter 336 into the mixing section 12. After passage through the filter member 336, the liquid component flows downward through a tubular portion 352 of the supply section 336, through the threaded hole 68 of mixing housing 69, and through the hole 123 of mixing end cap portion 96. In this way, the mixing section 12 may be filled with the contents of one or more single-ampules supply sections 326, with multiples of such sections 326 being inserted sequentially and emptied as described in reference to FIG. 13.

While an exemplary use of the second alternative first component supply section 326 is shown in FIG. 13, this section 326 may also be used in a number of ways. For example the liquid contents of one or more supply sections 326 may be used to fill the funnel 251 of FIG. 7, or in a number of other applications requiring the use of liquid from one or more ampules.

Figure 14:
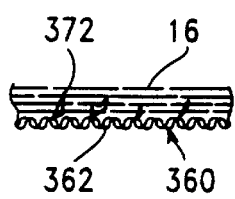
FIG. 14 is a fragmentary cross-sectional view showing a construction of a filter in the apparatus of FIG. 1 and FIG. 13.
Figure 15:
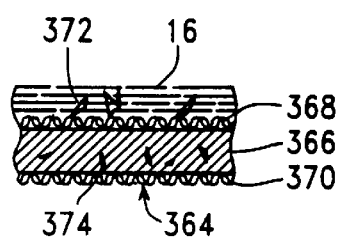
FIG. 15 is a fragmentary cross-sectional view showing an alternative construction of a filter in the apparatus of FIG. 1 and FIG. 13.

FIGS. 14 and 15 are fragmentary cross-sectional views showing alternate constructions which may be employed in the fabrication of filter 62 of FIG. 1 and of filter 336 of FIG.

13. In the example of FIG. 14, a filter 360 is formed using a single layer 362 of screen material. In the example of FIG. 15, a filter 364 includes a fibrous pad 366 extending between an upper layer 368 of screen material and a lower layer 370 of screen material. In either case, residue 372 formed when the ampule(s) 18 (shown in FIGS. 1 and 13) are opened are trapped above the filter 360, 364, while the liquid 16 is allowed to pass through the filter. The timely passage of liquid 16 through the filter 360, 364 is aided by the establishment of a vacuum below the filter, as explained above in reference to FIG. 1, or by the pressurization of air above the filter 360, 364 by depressing a plunger 340, as explained above in reference to FIG. 13. In the example of FIG. 15, small pieces 374 of residue are also entrapped within the fibrous pad 366.

The screen material and fibrous pads described above are preferably inert in the presence of the liquid component of the bone cement being mixed. Satisfactory results have been obtained using the configuration of FIG. 15 with a 250-micron filter formed of polypropylene woven cloth screen on each side of a cotton pad.

Referring again to FIG. 1, the first component supply section 10 and mixing section 12 are preferably shipped together, but in a disconnected relationship, with the ampules 18 within the supply section 10, and with the powder component 20 within the mixing section 12. Both the supply section 10 and the mixing section 12 are sterilized and hermetically sealed.

Figure 16:
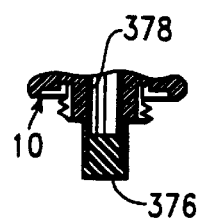
FIG. 16 is a fragmentary longitudinal cross-sectional view of a lower portion of the supply section in the apparatus of FIG. 1 in a condition of preparation for shipment.
Figure 17:
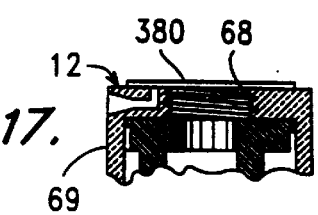
FIG. 17 is a fragmentary longitudinal cross-sectional view of an upper portion of the mixing section in the apparatus of FIG. 1 in a condition of preparation for shipment.

FIG. 16 is a fragmentary longitudinal cross-sectional view of the lower portion of supply section 10 prepared for shipment. An elastomeric stopper 376 is inserted within the hole 378 extending below the filter 62 (shown in FIG. 1) to maintain sterile conditions within the section 10. This stopper 376 is removed before the supply section 10 and the mixing section 12 are joined into the configuration of FIG. 1. FIG. 17 is a fragmentary longitudinal cross-sectional view of the upper portion of mixing section 12 prepared for shipment. An adhesive label 380 is attached to the upper end of the housing 69, extending across the threaded hole 68. This label 380 is also removed before the supply section 10 and the mixing section 12 are joined. As previously described in reference to FIGS. 1 and 4, the opposite end the mixing section 12 is sealed by means of a of elastomeric diaphragm seal 125, which is subsequently broken by a shaft 182 used to move the piston 102 so that mixed cement is dispensed from the mixing section 12.

Figure 18:
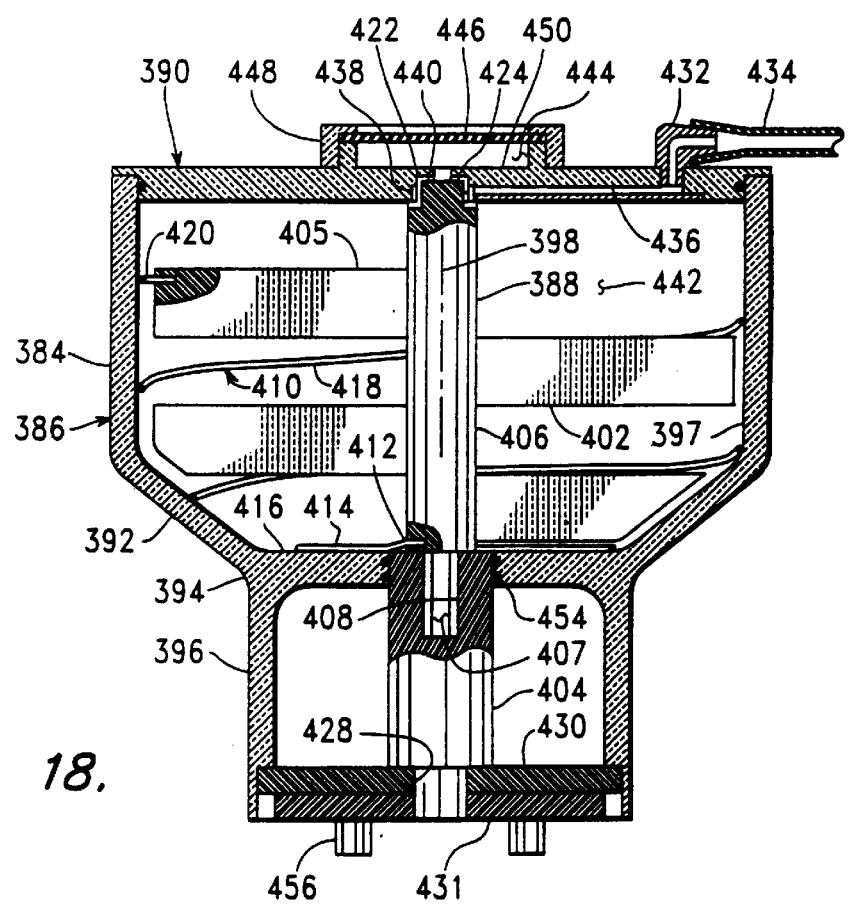
FIG. 18 is a longitudinal cross-sectional view of an alternative mixing section built in accordance with the present invention.

FIG. 18 is a longitudinal cross-sectional view of an alternative mixing section 384, built in accordance with the present invention, including a housing 386, a rotor 388 and a removable top 390. This alternative mixing section 384 is preferably used in number of surgical procedures, such as knee replacement, which are preferably performed using bone cement taken from a mixing bowl with a spatula, instead of using bone cement dispensed through a dispensing tube.

The housing 386 includes a bowl-shaped portion 392 extending upward from an intermediate level 394 and a hollow cylindrical portion 396 extending downward from the intermediate level 394. An internal surface 397 of the bowl-shaped portion 392 is formed as a surface of revolution about an axis 398. That is, all points at the same vertical distance (in the direction of arrow 400) along the surface 392 are the same radial distance from the axis 398.

The rotor 388 includes a paddle portion 402, rotatable within the bowl shaped portion 392 about an axis of rotation coaxial with the axis 398, and a drive shaft portion 404 rotatable within the hollow cylindrical portion 396 about an axis of rotation also coaxial with the axis 398. The paddle portion 402 includes a number of paddles 405 extending outward in alternating directions from a central cylinder 406. The paddle portion 402 and the drive shaft portion 404 are coupled to turn together by means of a hexagonally-shaped pin portion 407 of the paddle portion 402, which extends downward into a hexagonally-shaped hole 408 within the shaft portion 404. A spring member 410 extends from a lower connection 412 with the paddle portion 402 through a spiral spring portion 414 along the flat lower inner surface 416 of the bowl shaped portion 392, and upward through a modified helical spring portion 418 along the inner surface 397 to an upper connection 420 with the paddle portion 402. Within the modified helical spring portion 418, modifications are made to a helical configuration are made to accommodate variations in the radius of the inner surface 397 from the axis 398. An upper end cylinder 422 of the paddle portion 402 is rotatably mounted within a hole 424 in the removable top 390. The drive shaft portion 404 is rotatably mounted in a hole 426 within the housing 386 and in a hole 428 within a bearing plate 430 within a lower bearing plate 430 extending within the hollow cylindrical portion 396. A drive input wheel 431 is fastened to the drive shaft portion 404 to turn therewith.

The removable top 390 includes a connection 432 to a vacuum hose 434 and an internal air path 436 to an annular groove 438. A number of grooves 440 within the upper end cylinder 422 connect the annular groove 438 with both a mixing chamber 442 within the bowl shaped portion 392 and with a vacuum indicating chamber 444. The upper surface of the vacuum indicating chamber 444 is formed by a flexible disk 446, which is held in place by means of a retaining ring 448. Thus, when air is evacuated through the hose 434, air flows from both the mixing chamber 442 and the vacuum indicating chamber 444 through the grooves 440 in the upper end cylinder 422, around the annular ring 438, along the internal air path 438, and through the connector 432 into the hose 434. The resulting evacuation of the vacuum indicating chamber 444 causes the visible downward deflection of the flexible indicating disk 446, which is preferably composed of a translucent elastomeric material, so that a pattern on an underlying surface 450 is revealed with this downward deflection, while otherwise being hidden.

Referring to FIGS. 1 and 18, the alternative mixing section 386 is preferably shipped with the mixing chamber 442 containing an appropriate amount of the powder component (not shown) of bone cement. Sealing is accomplished through the use of an upper elastomeric ring 452 and a pair of lower elastomeric rings 454. When bone cement is to be mixed, the mixing section 386 is slid downward into place on the mixing base 14, with hollow cylindrical portion 396 extending into the receiving ring 146 of the clamping mechanism 86, and with the drive pins 456 extending downward from drive wheel 431 engaging the transverse slot 144 in the drive wheel 140. The clamping mechanism 86 is used to grip the cylindrical portion 396 in the manner previously described in reference to FIGS. 1 and 3. Next, with the top 390 removed, an appropriate amount of the liquid component (not shown) of bone cement is added to the powder within the mixing chamber 442. One or more of the alternative first component supply sections 326 may readily be used for this purpose. Next, the top 390 is replaced on the housing 386, and a vacuum within the mixing chamber 442 is drawn through the hose 434. The mixing process is started by the depression of button 212 and is performed as described above in reference to FIGS. 1

AND 5. When this process is complete, the vacuum in mixing chamber 442 is released, the top 390 is removed, and the mixed cement is removed by means of a spatula or other hand-held instrument.

While the invention has been described in its preferred forms or embodiments with some degree of particularity, it is understood that this description has been given only by way of example and that numerous changes in the details of construction, fabrication and use, including the combination and arrangement of parts, may be made without departing from the spirit and scope of the invention.

I claim:

1. Apparatus for dispensing a liquid component of a mixture, with said liquid component being held within an ampule, into a mixing chamber, wherein said apparatus comprises:

a supply section housing;

ampule holding means for holding said ampule within said supply section housing;

ampule opening means for opening said ampule within said ampule holding means to release said liquid component therein; and a dispensing section including a tube for dispensing said liquid component into said mixing chamber, and a filter extending across said tube, preventing passage therethrough of residue from walls of said ampule after opening while permitting passage therethrough of said liquid component, wherein said filter includes first and second sheets of screen material and a fiber pad extending between said first and second sheets of screen material.

2. Apparatus for dispensing a liquid component of a mixture, with said liquid component being held within an ampule, into a mixing chamber, wherein said apparatus comprises:

a supply section housing extending around said ampule;

ampule holding means for holding said ampule within said supply section housing;

ampule opening means for opening said ampule within said ampule holding means to release said liquid component therein; and a dispensing section including a tube for dispensing said liquid component into said mixing chamber, wherein said dispensing section extends around said ampule;

a filter extending across said tube, preventing passage therethrough of residue from walls of said ampule after opening while permitting passage therethrough of said liquid component and wherein said supply section housing includes an externally visible member which is deflected by a vacuum established within said mixing chamber when said liquid component is pulled through said filter.

3. The apparatus of claim 2, wherein said visible flexible member is translucent;

said supply section housing includes an indication surface underlying said visible flexible member, with said indication surface including an indication pattern, a central portion of said visible flexible member is held against said indication surface, visually revealing said indication pattern through said visible flexible member when a vacuum is present within said supply section housing, said visible flexible member is held away from said indication surface when a pressure level within said supply section housing is equal to an ambient pressure on a side of said visible flexible member opposite said supply section housing.

4. Apparatus for dispensing a liquid component of a mixture, with said liquid component being held within an ampule, into a mixing chamber, wherein said apparatus comprises:

a supply section housing;

ampule holding means for holding said ampule within said supply section housing;

ampule opening means for opening said ampule within said ampule holding means to release said liquid component therein wherein said ampule opening means includes a sliding member movable into said ampule as said ampule is held within said ampule holding means, and a lever engaging said sliding member to move said sliding member into said ampule; and a dispensing section including a tube for dispensing said liquid component into said mixing chamber.

5. Apparatus for dispensing a liquid component of a mixture, with said liquid component being held within an ampule, into a mixing chamber, wherein said apparatus comprises:

a supply section housing;

ampule holding means for holding said ampule within said supply section housing;

ampule opening means for opening said ampule within said ampule holding means to release said liquid component therein wherein said ampule opening means includes a turnable screw movable into said ampule as said ampule is held within said ampule holding means; and a dispensing section including a tube for dispensing said liquid component into said mixing chamber.

6. Apparatus for dispensing a liquid component of a mixture, with said liquid component being held within an ampule, into a mixing chamber, wherein said apparatus comprises:

a supply section housing;

ampule holding means for holding said ampule within said supply section housing wherein said ampule holding means includes means for holding three ampules in a triangular pattern;

ampule opening means for opening said ampule within said ampule holding means to release said liquid component therein, wherein said ampule opening means includes an ampule opening member movable between a first and second of said ampules, with said ampule opening member including a pin portion movable into a third of said ampules and a cylinder portion having an edge movable into said first and second ampules, with said cylinder portion being larger in diameter than said pin portion and coaxial with said pin portion; and a dispensing section including a tube for dispensing said liquid component into said mixing chamber.

7. The apparatus of claim 6, wherein said ampule opening member is mounted to slide into contact with said ampules, and said apparatus additionally includes a lever engaging said ampule opening member to move said ampule opening member into said ampules.

8. The apparatus of claim 6, wherein said ampule opening member includes an externally threaded surface engaging an internally threaded surface of a hole in said supply section housing.

9. Apparatus for mixing a two-component cement, wherein said apparatus comprises:
- a mixing housing;
- a mixing rotor mounted to rotate about an axis of rotation within said mixing housing;
- a drive base including clamping means releasably engaging a first end of said mixing housing, and rotor drive means releasably engaging said mixing rotor; and
- a liquid component supply section including a supply section housing, ampule holding means for holding an ampule within said supply section housing; ampule opening means for opening said ampule within said ampule holding means to release a liquid component therein, and a dispensing section including a tube extending into said mixing housing for dispensing said liquid component into said mixing housing.

10. The apparatus of claim 9, wherein said dispensing section additionally includes a filter extending across said tube, preventing passage therethrough of residue from walls of said ampule after opening while permitting passage therethrough of said liquid component.

11. The apparatus of claim 9, wherein said dispensing section additionally includes an intermediate cap including attachment means for releasably attaching a second end of said mixing housing, with said second end being opposite said first end thereof.

12. The apparatus of claim 11, wherein
- said apparatus includes a first air path extending between a mixing chamber within said mixing housing and an external vacuum connection, and a second air path extending between said mixing chamber and a chamber within said supply section housing;
- said dispensing section includes a filter extending across said tube extending into said mixing housing for dispensing said liquid component into said mixing housing; and
- said supply section housing includes an externally visible flexible member which is deflected by a vacuum established within said mixing chamber when said liquid component is pulled through said filter.

13. The apparatus of claim 9, wherein said ampule opening means includes:
- a sliding member movable into said ampule as said ampule is held within said ampule holding means; and
- a lever engaging said sliding member to move said sliding member into said ampule.

14. The apparatus of claim 9, wherein said ampule opening means includes a screw movable into said ampule as said ampule is held within said ampule holding means.

15. The apparatus of claim 9, wherein
- said ampule holding means includes means for holding three ampules in a triangular pattern, and
- said ampule opening means includes a sliding member movable between a first and second of said ampules, with said sliding member including a pin portion movable into a third of said ampules and a cylinder portion having an edge movable into said first and second ampules, with said cylinder portion being larger in diameter than said pin portion and coaxial with said pin portion, wherein said apparatus additionally includes a lever engaging said sliding member to move said sliding member into said ampules.

16. The apparatus of claim 9, wherein
- said ampule holding means includes means for holding three ampules in a triangular pattern, and
- said ampule opening means includes a screw member movable between a first and second of said ampules, with said screw member including a pin portion movable into a third of said ampules and a cylinder portion having an edge movable into said first and second ampules, with said cylinder portion being larger in diameter than said pin portion and coaxial with said pin portion, with said screw member including an external threaded surface engaging an internal threaded surface of a hole in said supply section housing, and with said screw member extending outward from said supply section housing to be turned by means of handle.

17. The apparatus of claim 9, wherein said rotor drive means includes:
- a drive shaft mounted to rotate within said drive base;
- a drive coupling mounted on said drive shaft, extending outward from said drive base to releasably engage said mixing rotor; and
- a motor rotating said drive shaft in response to an electrical input.

18. The apparatus of claim 17, wherein said rotor drive means additionally includes first control means generating said electrical input to rotate said motor sequentially in opposite directions, with rotation in each of said opposite directions occurring for a predetermined time.

19. The apparatus of claim 18, wherein
- said mixing housing includes a hollow cylindrical portion extending longitudinally parallel to said axis of rotation, and
- said mixing rotor includes a first paddle extending longitudinally parallel to said axis or rotation within said hollow cylindrical portion.

20. The apparatus of claim 19, wherein said mixing rotor additionally includes a second paddle extending longitudinally parallel to said axis of rotation within said hollow cylindrical portion, with said first and second paddles being displaced through different radial distances from said axis of rotation.

21. The apparatus of claim 20 wherein said mixing rotor additionally includes a flexible member scraping an interface of said hollow cylindrical portion.

22. The apparatus of claim 21, wherein said flexible member is a helical spring.

23. The apparatus of claim 9, wherein said rotor drive means additionally includes:
- switching means for starting and stopping operation of said rotor drive means; and
- second control means generating a sequence of audible messages indicating an elapsed time following the operation of said switching means to start operation of said rotor drive means.

24. The apparatus of claim 9, wherein said clamping means includes:
- a receiving ring for receiving said first end of said mixing housing;
- a locking ring rotatably mounted on said receiving ring; and
- a gripping member moved into engagement with said first end of said mixing housing within said receiving ring as said locking ring is rotated from an unlocking position to a locking position.

25. The apparatus of claim 9, wherein
- said mixing housing includes a hollow cylindrical portion extending longitudinally parallel to said axis of rotation, and said mixing rotor includes a first paddle extending longitudinally parallel to said axis of rotation within said hollow cylindrical portion.

26. The apparatus of claim 25, wherein said mixing rotor additionally includes a second paddle extending longitudinally parallel to said axis of rotation within said hollow cylindrical portion, with said first and second paddles being displaced through different radial distances from said axis of rotation.

27. The apparatus of claim 26, wherein said mixing rotor additionally includes a flexible member scraping an internal surface of said hollow cylindrical portion.

28. The apparatus of claim 27, wherein said flexible member is a helical spring.

29. The apparatus of claim 25, wherein said mixing rotor additionally includes a first end cap at a first end thereof, a second end cap at a second end thereof, with said second end being opposite said first end, and a piston slidable along said first paddle in contact with an internal surface of said hollow cylindrical portion between said first and second end caps, with said first end cap including an access hole for moving said piston, and with said second end cap including a dispensing hole through which said cement is dispensed, and said mixing housing additionally includes a housing end cap extending across an end thereof, outwardly adjacent said second end cap, with said mixing housing including a housing cap hole through which said liquid component is dispensed into said mixing housing and through which said cement is dispensed from said mixing housing.

30. The apparatus of claim 29, wherein said mixing rotor additionally includes a flexible scraping member scraping an internal surface of said hollow cylindrical portion.

31. The apparatus of claim 30, wherein a first end of said flexible scraping member is attached to said piston, said flexible member extending therefrom to said second end cap, and with said flexible member collapsing between said piston and said second end cap as said piston is moved toward said second end cap.

32. The apparatus of claim 31, wherein said flexible member collapses into an annular groove, allowing said pistol be brought into contact with said second end cap.

33. The apparatus of claim 31, wherein said flexible member is a helical spring.

34. The apparatus of claim 29, wherein said first end cap includes a breakable sealing member extending across said access hole.

35. The apparatus of claim 29, wherein said mixing apparatus additionally includes a dispensing tube attachable to said housing end cap to extend outward from said housing; and said piston additionally includes a removable plug which is movable within and along said dispensing tube.

36. The apparatus of claim 29, wherein said mixing apparatus additionally includes a dispensing device into which said mixing housing is placeable following removal of said drive base therefrom, with said dispensing device including:

holding means for holding said mixing housing;

a piston driving shaft; and shaft drive means for moving said piston driving shaft through said access hole into contact with said piston and for moving said piston in contact with said piston driving shaft between said first and second end caps.

37. The apparatus of claim 36, wherein said mixing apparatus additionally includes a dispensing tube attachable to said housing end cap to extend outward from said housing; and said piston additionally includes a removable plug;

said piston driving shaft is hollow; and said mixing apparatus additionally includes pushrod insertable within said piston driving shaft to push said removable plug within and along said dispensing tube.

38. The apparatus of claim 36, wherein said first end cap includes a breakable sealing member extending across said access hole, with said breakable sealing member being broken by said piston driving shaft.

39. Apparatus for dispensing contents of a sealed ampule, with said apparatus comprising:

a housing including a lower receptacle surrounding lower portion of said ampule, ampule opening means including a tip movable into said receptacle;

a piston including an upper receptacle surrounding an upper portion of said ampule;
with said piston being movable downward into said housing to increase air pressure within said upper receptacle;

a dispensing hole extending downward through a lower portion of said housing from said lower receptacle; and a filter extending across said dispensing hole, with said filter preventing passage therethrough of residue from walls of said ampule after said ampule is opened, while allowing passage therethrough of said contents from said ampule as air pressure is increased above said contents by depressing said piston, wherein said filter includes first and second sheets of screen material extending across said dispensing hole, and a fibrous pad extending between said first and second sheets of screen material.

40. Apparatus for dispensing contents of a sealed ampule, with said apparatus comprising:

a housing including a lower receptacle surrounding a lower portion of said ampule, ampule opening means including a tip movable into said receptacle, wherein said ampule opening means includes a screw having external threads engaging internal threads within said housing, with said screw extending outward from said housing to a wheel attached thereto;

a piston including an upper receptacle surrounding an upper portion of said ampule;
with said piston being movable downward into said housing to increase air pressure within said upper receptacle;

a dispensing hole extending downward through a lower portion of said housing from said lower receptacle; and a filter extending across said dispensing hole, with said filter preventing passage therethrough of residue from walls of said ampule after said ampule is opened, while allowing passage therethrough of said contents from said ampule as air pressure is increased above said contents by depressing said piston.

* * * * *

UNITED STATES PATENT AND TRADEMARK OFFICE
CERTIFICATE OF CORRECTION

PATENT NO. : 6,176,607 B1
DATED : January 23, 2001
INVENTOR(S) : Hajianpour

It is certified that error appears in the above-identified patent and that said Letters Patent is hereby corrected as shown below:

Column 4,
Line 19, cancel "including those".
Line 25, "be" should read -- by --.

Column 5,
Line 25, "therefor" should read -- therefore --.

Column 6,
Line 9, after "invention" insert -- is --.

Column 7,
Line 34, after "used" insert -- with --.

Column 8,
Line 56, cancel "a" (second occurrence).

Column 9,
Line 63, cancel "be".

Column 11,
Line 10, after "16" cancel ",".
Line 14, "the" should read -- they --.

Column 12,
Line 52, "forfeeding" should read -- for feeding --.

Column 15,
Line 5, cancel "As".
Line 5, "the" should read -- The --.
Line 20, after "in" insert -- the --.

Column 19,
Line 37, begin a new paragraph with "FIG. 17".
Line 42, after "end" insert -- of --.
Line 43, cancel "a of".
Line 43, after "of" insert -- an --.

UNITED STATES PATENT AND TRADEMARK OFFICE
CERTIFICATE OF CORRECTION

PATENT NO. : 6,176,607 B1
DATED : January 23, 2001
INVENTOR(S) : Hajianpour

It is certified that error appears in the above-identified patent and that said Letters Patent is hereby corrected as shown below:

Column 20,
Line 16, cancel "are made" (first occurrence).

Column 21,
Line 1, "AND" should read -- and --.

Column 24,
Line 12, after "of" insert -- a --.
Line 32, "or" should read -- of --.

Column 25,
Line 37, after "piston," insert -- with --.
Line 44, after "pistol" insert -- to --.

Column 26,
Line 9, after "includes" insert -- a --.
Line 19, after "surrounding" insert -- a --.

Signed and Sealed this

Twenty-second Day of January, 2002

Attest:

Attesting Officer

JAMES E. ROGAN
Director of the United States Patent and Trademark Office